United States Patent [19]

Lorch

[11] Patent Number: 4,630,643
[45] Date of Patent: Dec. 23, 1986

[54] VALVE, PARTICULARLY MIXING VALVE

[75] Inventor: Werner Lorch, Schramberg, Fed. Rep. of Germany

[73] Assignee: Hans Grohe GmbH & Co. KG, Fed. Rep. of Germany

[21] Appl. No.: 544,872

[22] Filed: Oct. 24, 1983

[30] Foreign Application Priority Data

Oct. 23, 1982 [DE] Fed. Rep. of Germany ....... 3239301

[51] Int. Cl.$^4$ .................... F16K 21/00; F16K 11/072
[52] U.S. Cl. ................................ 137/597; 137/625.41
[58] Field of Search ............... 137/597, 616.3, 788, 137/615, 616, 269; 251/149.6

[56] References Cited

U.S. PATENT DOCUMENTS 2,829,645  4/1958  Matteson .................... 137/597 X
2,992,657  7/1961  Weddendorf, Jr. ........... 137/597 X

FOREIGN PATENT DOCUMENTS 815433   8/1951  Fed. Rep. of Germany .
1786719  5/1959  Fed. Rep. of Germany .
1913934  4/1965  Fed. Rep. of Germany .
1428407  9/1969  Fed. Rep. of Germany .
7532166 11/1976  Fed. Rep. of Germany .
2741832  3/1979  Fed. Rep. of Germany .
2922580 12/1980  Fed. Rep. of Germany .
2947720  7/1981  Fed. Rep. of Germany .
3025023  1/1982  Fed. Rep. of Germany .
620136  11/1980  Switzerland .

Primary Examiner—Martin P. Schwadron
Assistant Examiner—John S. Starsiak, Jr.
Attorney, Agent, or Firm—Steele, Gould & Fried

[57] ABSTRACT

A valve contains a connection for connecting to a tube of a supplemental shower head or spray nozzle, the connection preferably containing a check valve. In the case of the preferred embodiment, the connection for the supplemental apparatus is arranged in the handle of the operating lever connected to a spherical plug valve. The water is supplied to the handle through the hollow connecting rod, from the interior of the spherical plug.

8 Claims, 1 Drawing Figure

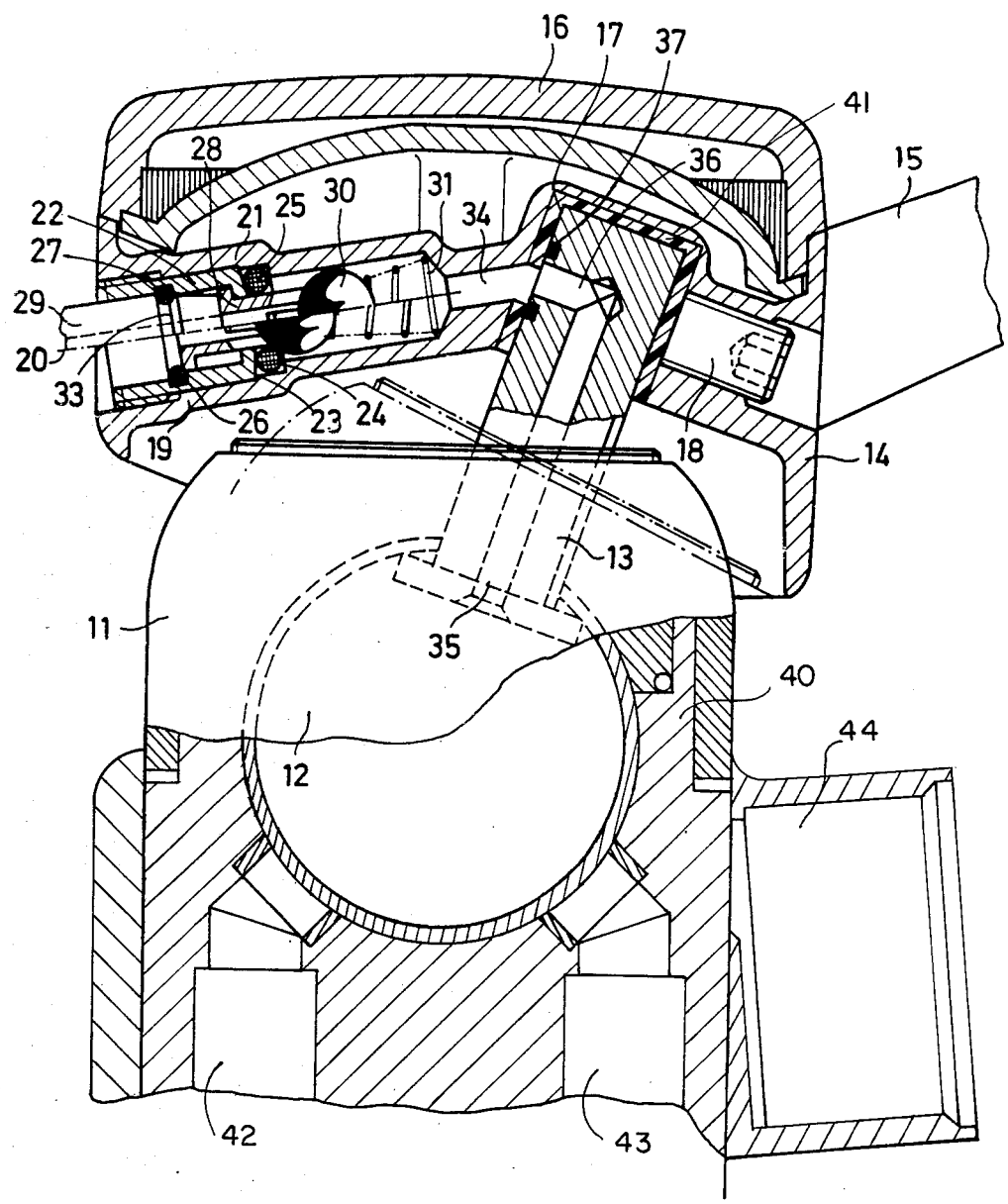

VALVE, PARTICULARLY MIXING VALVE

BACKGROUND OF THE INVENTION

1. Field of the Invention

The invention relates to a valve, particularly a mixing valve, with a valve casing, a water outlet and at least one water inlet.

2. Prior Art

It is known to connect a dental syringe to the outlet end of a mixing valve with the aid of an adapter. When the dental syringe is attached, the water tap can no longer be normally used.

It is also known (DOS No. 30 25 023) to connect a dental syringe to the shower tube of a bath or shower bath fixture. For this purpose, the normal shower must firstly be disconnected and then the dental syringe connected. Here again, it is no longer possible to use the shower tube normally, when the dental syringe is connected.

It is also known (DOS No. 29 47 720) to attach a three-way valve to the outlet end of a water tap. This three-way valve has two water outlets, it being possible to connect a feed tube for a dental syringe to one water outlet and a so-called bubbler to the other water outlet. Such an additional three-way valve naturally has a prejudicial effect and significantly impairs the appearance of a mixing valve.

In addition, dental syringes are known, which have their own water container, which is filled prior to operation and supply the liquid with the aid of a pump.

SUMMARY OF THE INVENTION

The object of the invention is to permit a very simple connection and operation of a dental syringe, a toothbrush, or similar supplementary apparatus, without the appearance and function of the valve fitting being impaired. Moreover, this must be accomplished with only the smallest possible change in the construction of the fitting.

According to the invention this object is achieved in that a valve of the aforementioned type has a connection for a supplementary apparatus, provided with a quick-action coupling device, leading in to the interior of the valve casing. This makes it possible to simply connect to the valve a supplementary apparatus, for example a dental syringe, without the valve, particularly a mixing valve having its normal use impaired. It is particularly favourable if the quick-action coupling device is a plug-in coupling.

No additional control element is required for operating the supplementary apparatus, because the passage of water through the apparatus can be controlled with the aid of the conventional control element of the valve. It is naturally also possible to use a dental syringe with a simple shutoff valve, for example in the tube connecting the dental syringe to the valve. In this case, the dental syringe can be continuously connected to the mixing valve.

However, it is particularly advantageous if, according to another feature of the invention, the connection has a check valve. In this case, after use, the supplemental apparatus can easily be detached.

According to a further development, in the case of a mixing valve, the connection leads into an area of the valve which carries mixed water. As a result, it is possible to set and select the water supply (both temperature and flow rate) with the aid of the normal mixing valve operatons.

In order to permit the connection of the supplemental apparatus in the case of already existing valves or mixing valves, the invention also proposes to lead the connection for the supplementary apparatus at least partly through the control element. In this case, it is merely necessary to replace one control element by another. The possibility of easy reequipment is also provided. For example, one hand-operated mixing valves are known, in which a control member is connected to a handle with the aid of a control element. The latter, which can be shaped like a rod or lever, is longitudinally bored according to the invention and the bore outlet on the valve inside issues into the valve mixing area. The connection for the supplementary apparatus is then arranged on the lever handle.

However, it is also possible for an optionally flexible line to lead from the mixing area to a connection for the supplementary apparatus.

In order that the visual appearance and function of the mixing fixture are minimally impaired, the invention also provides for the connection to issue on to the back of the valve and/or handle. In this case, the visual appearance is not impaired in the slightest. It is also advantageously possible for the connection to be constructed in recessed manner, so that no part thereof projects above the outer contour of the mixing fixture. This is particularly advantageous in permitting easier cleaning of the mixing valve.

It is particularly advantageous to use the invention in the case of a single lever-operated mixing valve with a spherical plug (as shown in Applicant's U.S. Pat. No. 4,449,551), in which case the connection leads into the spherical plug. This is a particularly favorable and simple embodiment of the connection and it is in particular possible to use a hollow connecting rod between the lever handle and the spherical plug and this serves as a line. A thermally insulating seal is then advantageously inserted between the connecting rod and the lever handle.

BRIEF DESCRIPTION OF THE DRAWING

Further features, details and advantages of the invention can be gathered from the following description of a preferred embodiment thereof, as well as from the drawing. This drawing shows a section through the connection of a spherical plug to a lever handle.

DETAILED DESCRIPTION OF THE PREFERRED EMBODIMENTS

The drawing shows a cap nut 11, which seals at the top the lower part of a valve and in whose interior is arranged a spherical plug 12. The spherical plug 12 cooperates with water inlet ports 42, 43 and outlet port 44. The handle 14 is pivotably mounted with respect to the cap nut 11 of the valve casing 40. The solid lines of the FIGURE show a first relative position between the cap nut 11 and the handle 14. The phantom line depiction of the top of the cap nut 11 illustrates a second relative position of the cap nut 11 and the handle 14, although as noted, the cap nut 11 is fixed in position and the handle 14 is pivoted relative to the fixed cap nut.

The spherical plug 12 is connected via a connecting rod 13 to the handle 14, on to which is shaped in one piece on the right-hand side of the drawing, an operating lever 15. Handle 14 is terminated upwards by a cover 16. The lower end of the connecting rod 13 engages into the interior of the spherical plug 12, while its upper end engages in a corresponding blind bore 17 in handle 14. Connecting rod 13 is fixed in blind bore 17 with the aid of a screw 18. Further details of such valves may be seen in Applicant's U.S. Pat. No. 4,449.551, which details do not form a part of this invention.

Within the handle 14 is provided a plug-in coupling 19 for the connection of a supplementat apparatus, which is not shown in the drawing. The drawing shows the plug-in coupling above its center line 20 in the open position and below the center line 20 in the closed position. The plug-in coupling 19 contains an outer part 21, into which is screwed a bush 22 from the left-hand side of the drawing. A packing ring 25 is placed between the inner end face 23 of bush 22 and a shoulder 24 of outer part 21. On the inside of bush 22 is provided an annular groove 26, in which is placed a second packing ring 27. In bush 22 is placed a guide member 28, whose front side can be moved to the right by a connecting member 29 insertable into the plug-in coupling 19. With its right-hand end, in the sense of the drawing, guide member 28 engages with a ball 30, which is under the bias of a spring 31. If the connecting member 29 is removed from the plug-in coupling 19, the ball 30 engages on packing ring 25, which represents the sealing of the plug-in coupling 19.

The connecting member 29, which is connected to the supplemental apparatus by a tube (not shown), has in its front end an annular notch 33, which brings about engagement together with the packing ring 27.

The interior of plug-in coupling 19 is connected by means of a through bore 34 with the blind bore 17. Connecting rod 13 has a longitudinally directed blind bore 35, which passes into a radially directed bore 36. Radial bore 36 is arranged in such a way that, when the connecting rod 13 is inserted, it coincides with the opening of the through-bore 34. A packing ring 37 is arranged over the opening of bore 36.

It would also be possible to thermally insulate by means of a seal 41 the complete space between the connecting rod 13 and the blind bore 17.

When the mixing valve shown in the drawing is operating, liquid passes out of the interior of spherical plug 12, through bores 35, 36, 34 into the interior of the plug-in coupling 19, from where it can pass through the interior of connecting member 29 to the supplemental apparatus, when ball 30 is displaced to the right. When the connecting member 29 is extended, the connection formed by the plug-in coupling 19 is sealed in a liquid-tight manner.

It is pointed out that the preferred embodiment of the invention shown in the drawing can be used in a known mixing valve, without any modification thereto. It is merely necessary to modify handle 14 by inserting plug-in coupling 19 and the connecting rod 13 through bores 35, 36, the rest of the mixing valve remaining unchanged. It can also be seen that the connection or plug-in coupling 19 is arranged on the side of handle 14 remote from the actual operating lever 15. As operating lever 15 is normally at the front, the connection for the dental syringe or other supplemental apparatus is located on the back of handle 14. Thus, the connection cannot be seen from the front, so that the visual impression of the mixing fitting is not impaired. It is also clear that if the connecting member 29 is removed from the plug-in coupling 19, the latter does not project over the outer contour of handle 14. This also ensures that the visual appearance is not impaired. In addition, the cleaning and care of the mixing fitting are in no way impaired.

What is claimed is:

1. A mixing valve for attachment to a water faucet or the like, comprising:
   a valve casing having a water outlet and two water inlets;
   a control member having an interior liquid mixing chamber rotatably mounted in said casing between said inlets and said outlet for mixing and controlling the water, said control member comprising a spherical plug valve;
   means for connecting a supplemental apparatus in communication with the interior of said mixing chamber, said means having a quick-action coupling means, and
   handle means interposed between the control member and said connecting means, said handle means being associated with said control member through a hollow rod, said rod engaging an opening in said control member and having a bore therethrough for communicating the mixing chamber and said connecting means, whereby fluid from said mixing chamber passes through said rod and connecting means to said supplemental apparatus.

2. The mixing valve of claim 1 wherein said rod engages the interior of said control member at one end and at the end engages a blind bore in said handle means.

3. The mixing valve of claim 2 wherein said connecting means is aligned with said blind bore of said handle means.

4. In a faucet having a ball-like control member, a handle means for controlling movement of said control member, a fluid mixing chamber, two liquid inlet means and an outlet means, a valve casing having a valve seat face of the same form as the control member, the control member and the housing having a common middle point about which said control member is rotatable relative to said housing said control member being between said inlet means and said outlet means so as to control the fluid between two said inlet means and said fluid mixing area, the improvement which comprises:
   means for connecting a supplemental apparatus in communication with the interior of said casing through said handle means, said connecting means having a quick-action coupling means, and
   handle means interposed between the control member and said connecting means, said handle means being connected by a hollow rod to the interior of said control member, said rod having a bore therethrough forming part of the passageway whereby fluid from said mixing chamber passes through said rod, to said connecting means and then to said supplemental apparatus.

5. The faucet of claim 4 wherein said connecting means includes a check valve.

6. A valve according to claim 1, wherein the quick-action coupling device comprises a plug-in coupling.

7. A valve according to claims 1 or 6, wherein the connection further comprises a check valve.

8. A valve according to claim 7, wherein an area in the interior of the valve casing carries water mixed from said water inlets, and the connection communicates with the area carrying the mixed water.

* * * * *